(12) United States Patent
Schmidt et al.

(10) Patent No.: US 6,582,916 B1
(45) Date of Patent: Jun. 24, 2003

(54) METAL ION-BINDING MASS MARKERS FOR NUCLEIC ACIDS

(75) Inventors: Gunter Schmidt, Cambridge (GB); Andrew Hugin Thompson, Ayr (GB); Robert Alexander W. Johnstone, Bebington (GB)

(73) Assignee: Aventis Research & Technologies GmbH & Co. KG, Frankfurt (DE)

( * ) Notice: Subject to any disclaimer, the term of this patent is extended or adjusted under 35 U.S.C. 154(b) by 0 days.

(21) Appl. No.: 09/743,748

(22) PCT Filed: Jul. 13, 1999

(86) PCT No.: PCT/GB99/02246

§ 371 (c)(1),
(2), (4) Date: Mar. 16, 2001

(87) PCT Pub. No.: WO00/02893

PCT Pub. Date: Jan. 20, 2000

(30) Foreign Application Priority Data

Jul. 13, 1998 (GB) .............................................. 9815166

(51) Int. Cl.$^7$ .......................... C12Q 1/68; G01N 33/00; G01N 24/00
(52) U.S. Cl. ............................. 435/6; 436/94; 436/173
(58) Field of Search .................. 436/173, 94; 536/25.3; 435/6

(56) References Cited

U.S. PATENT DOCUMENTS

| 5,237,101 | A | * | 8/1993 | Nicolaou et al. | .............. 568/28 |
| 5,494,793 | A | | 2/1996 | Schindele et al. | |
| 5,565,552 | A | | 10/1996 | Magda et al. | |
| 5,589,586 | A | * | 12/1996 | Holmberg | .................. 536/25.3 |
| 5,635,404 | A | * | 6/1997 | Wilson | ........................ 436/173 |
| 6,027,890 | A | * | 2/2000 | Ness et al. | ..................... 435/6 |
| 6,287,780 | B1 | * | 9/2001 | Schmidt et al. | ................. 435/6 |

FOREIGN PATENT DOCUMENTS

| EP | 0502723 | 9/1992 |
| WO | WO96/11937 | 4/1996 |
| WO | WO97/27327 | 7/1997 |
| WO | WO 99/32501 | 7/1999 |

* cited by examiner

*Primary Examiner*—Kenneth R. Horlick
(74) *Attorney, Agent, or Firm*—Pillsbury Winthrop LLP

(57) ABSTRACT

Provided is a method for characterising an analyte, which method comprises: a) providing a compound in which the analyte is attached by at cleavable linker to a mass marker relatable to the analyte; b) cleaving the mass marker from the analyte; and c) identifying the mass marker, thereby characterising the analyte, wherein the mass marker comprises a metal ion-binding moiety.

39 Claims, No Drawings

METAL ION-BINDING MASS MARKERS FOR NUCLEIC ACIDS

This application is the national phase of international application PCT/GB99/02246 filed Jul. 13, 1999 which designated the U.S. and that international application was published under PCT Article 21(2) in English.

This invention concerns compounds which comprise mass markers for detection by mass spectrometry. The invention relates to methods for characterising analytes, such as nucleic acids and other molecules, using markers that are cleavably detachable from their associated analyte and that are detectable by mass spectrometry. Specifically this invention relates to chemical entities that improve the sensitivity of detection by mass spectrometry of detachable mass labels.

PCT/GB98100 127 describes arrays of cleavable labels that are detectable by mass spectrometry which identify the sequence of a covalently linked nucleic acid probe. These mass labels have a number of advantages over other methods of analysing nucleic acids. At present commercially favoured systems are based on fluorescent labelling of DNA. Fluorescent labelling schemes permit the labelling of a relatively small number of molecules simultaneously, typically four labels can be used simultaneously and possibly up to eight. However the costs of the detection apparatus and the difficulties of analysing the resultant signals limit the number of labels that can be used simultaneously in a fluorescence detection scheme. An advantage of using mass labels is the possibility of generating large numbers of labels which have discrete peaks in a mass spectrum allowing similar numbers of distinct molecular species to be labelled simultaneously. Fluorescent dyes are expensive to synthesise whereas mass labels can comprise relatively simple polymers permitting combinatorial synthesis of large numbers of labels at low cost.

A critical feature of the mass labelling techniques disclosed in PCT/GB99/00127 is the design of mass markers. A number of features are required of a molecule that is to be a good mass marker. A marker should:

Be easily detachable from DNA.

Be fragmentation resistant in mass spectrometer.

Form a single ion peak in the mass spectrum.

Permit very sensitive detection.

Be easily distinguishable from background contamination, such as DNA, such that it can be clearly determined that a mass peak is from a mass label.

Be compatible with conventional automated oligonucleotide synthesisers.

Be compatible with existing mass spectrometry instrumentation without requiring physical modification.

A feature up to present of the analysis of nucleic acids by mass spectrometry is the need to condition the nucleic acid prior to analysis. This involves removing all metal ions, particularly magnesium and sodium as these readily form adducts with nucleic acids. These sample conditioning steps require additional preparation steps and instrumentation to allow automation of analysis. Indirect analysis of markers by mass spectrometry avoids many of the problems of direct analysis of, for example, DNA, whilst retaining the benefits of the mass spectrometer, such as high throughput, automation and high sensitivity.

However even with indirect labelling there is a need to ensure that there is little background contamination or that the labels are easily detectable over any background signals. It is thus desirable to provide mass markers that are detectable with high sensitivity over a background of contaminating material to reduce the requirements for sample conditioning and to simplify the use of mass labelling techniques. It is also desirable that mass markers are detected preferentially over background material.

A feature of the analysis of complex mixtures of analytes is competition during ionisation leading to suppression of certain ion peaks. In the use of multiple mass markers it is desirable to reduce these sorts of effects by providing an array of mass labels in which there is no competition during ionisation so that a high proportion of labels are ionised during mass spectrometry improving sensitivity and the signal to noise ratio.

It is an object of this invention to solve the above problems and to provide improved mass markers which are compatible with existing mass spectrometers particularly electrospray ionisation and tandem mass spectrometry, that have the desired features disclosed above.

It is also an object of this invention to provide compounds which have desirable features as mass labels which further simplify the manipulations of the molecules to which the are linked prior to being able to perform mass spectrometry.

Accordingly, the present invention provides a compound having the following formula:

N—L—M wherein N comprises a nucleic acid, L is either a direct bond between N and M or L comprises a cleavable linker, and M comprises a mass marker having a metal ion-binding moiety.

The invention further provides a method for characterising an analyte, which method comprises:

(a) providing a compound in which the analyte is attached by a cleavable linker to a mass marker relatable to the analyte, (b) cleaving the mass marker from the analyte; and (c) identifying the mass marker, thereby characterising the analyte.

wherein the mass marker comprises a metal ion-binding moiety.

The invention also provides use of a mass marker identifiable by mass spectrometry for the characterisation of an analyte, wherein the mass marker comprises a metal ion-binding moiety.

The mass labelled molecules used in the present invention have the following properties:

(1) The ability to bind to a metal ion to generate a charged species.

(2) Stability to permit participation in combinatorial synthesis of multiple distinct mass markers and stability in a conventional automated nucleic acid synthesiser.

(3) Fragmentation resistance under conditions within a mass spectrometer.

(4) Improved detection by mass spectrometry.

Thus the compounds and methods of this invention achieve preferential ionisation over background material through the binding of a metal ion, effectively pre-ionising the label prior to mass spectrometry.

This ion-binding feature also ensures that there is no competition for Ionisation between labels as it is relatively trivial to ensure that there are sufficient metal ions in the buffers that are used in the analytical protocols preceding mass spectrometry.

By pre-ionising the mass labels used in this invention very gentle ionisation conditions can be used in the mass spectrometer reducing the ionisation of contaminating material.

In this way the signal to noise ratio of mass spectrometry analysis steps is greatly improved.

A further feature of the metal ion binding mass markers is high sensitivity of detection. It is known that in typical ionisation procedures such as Electrospray Ionisation (ESI) and Matrix Assisted Laser Desorption Ionisation (MALDI) only about one in a thousand molecules ionise although accurate data for precise quantities are not available. MALDI is known to be worse in this respect than ESI. Despite this mass spectrometers achieve extraordinary levels of sensitivity. This is because the detection apparatus used is sensitive to the arrival of a single ion. The labels of this invention will be pre-ionised, potentially achieving much higher ionisation, of the order of 1 in 10 molecules. This further enhances the signal to noise ratio in the mass spectrometry detection and may also increase the sensitivity of detection by up to two orders of magnitude.

The various aspects of the invention will now be described in more detail.

As discussed above, an aspect of this invention provides a method for characterising an analyte, which method comprises:
(a) providing a compound in which the analyte is attached by a cleavable linker to a mass marker relatable to the analyte;
(b) cleaving the mass marker from the analyte, and
(c) identifying the mass marker, thereby characterising the analyte.
wherein the mass marker comprises a metal ion-binding moiety.

In the methods of the present invention, the analyte is not particularly limited and can be any analyte or molecule of interest, such as a nucleic acid or other molecule. Typically the analyte comprises a biological molecule. In preferred embodiments of the present invention, the biological molecule is selected from a protein, a polypeptide, an amino acid, a nucleic acid (e.g. an RNA, a DNA, a plasmid, a nucleotide or an oligonucleotide), a nucleic acid base, a pharmaceutical agent or drug, a carbohydrate, a lipid, a natural product and a synthetic compound from an encoded chemical library. When the analyte comprises a nucleotide, oligonucleotide or nucleic acid, the nucleotide, oligonucleotide or nucleic acid may be natural, or may be modified by modifying a base, sugar and/or backbone of the nucleotide, oligonucleotide or nucleic acid. In the compounds of the present invention, the analyte is a nucleic acid, and may be any type of nucleic acid. Preferably, the nucleic acid is of a type as defined above.

There are a variety of molecules that are well known in the art which bind metal ions and which are appropriate for use in mass labels. Typical molecules include porphyrins, crown ethers, hexahistidine and a variety of bidentate ligands used to chelate metal ions in solution such as EDTA (Ethylenediaminetetraacetic acid). Preferred metal ion chelating groups are those which bind monovalent ions, although entities which bind divalent ions such as EDTA can be employed with this invention, if desired.

The ion binding molecules used in this invention typically have a series of nucleophilic groups in positions on the molecule where they can co-ordinate a metal ion. Ion binding molecules can be tuned to bind specifically to particular ions by altering the spacing and co-ordination of nucleophilic groups within the chelating entity.

Crown ethers are favoured for use with this invention as ethers are generally relatively fragmentation resistant and are moderately soluble. Furthermore their structures can be relatively easily tuned to bind certain metal ions with high specificity.

The metal ion employed is not especially limited. Preferred metal ions are monovalent, divalent, or trivalent. It is further preferred that the metal ions are transition metal ions or belong to groups IA, IIA or IIIA of the periodic table. Particularly preferred metal ions include $Li^+$, $Na^+$, $K^+$, $Mg^{2+}$, $Ca^{2+}$, $Sr^{2+}$, $Ba^{2+}$, and $Al^{3+}$. The presence of a metal ion on the marker increases the sensitivity of detection.

The mass markers used in the present invention are not particularly limited. In preferred embodiments of the present invention, mass markers disclosed in PCT/GB98/00127, PCT/GB98/03842, and GB 9826159.7 can be employed. The content of these applications is incorporated by reference. PCT/GB98/00127 and PCT/GB98103842 disclose poly-ether mass markers which are thermally stable, chemically inert and fragmentation resistant compounds, and which can be substituted with a variety of groups to alter properties such as solubility and charge. These mass markers are also preferred for use in the present invention and the content of this application is incorporated by reference. GB 9826159.7 discloses markers which comprise two components, which may be poly-ethers, which are analysed by selected reaction monitoring. These are particularly preferred mass markers for use in the present invention. Mass marker groups that can be detected by more than one detection means may also be desirable as with, for example, a fluorescent marker that incorporates a radioisotope in its linker and that is detectable by mass spectrometry. Mass markers of this kind are refereed to as 'multi-mode reporter' groups.

When the mass marker comprises an oligoether or a polyether, the oligoether or polyether may be a substituted or unsubstituted oligo- or poly-arylether. The oligoether or polyether preferably comprises one or more fluorine atom or methyl group substituents, or one or more $^2H$ or $^{13}C$ isotopic substituents.

PCT/GB98/00127 discloses the use of substituted polyethers. These are highly favoured for use as mass markers with this invention. Poly-ethers are highly resistant to fragmentation. A polymer system is ideal for the purposes of generating large numbers of well spaced mass markers, particularly aryl ethers. These can be readily substituted with a variety of groups to change properties such as solubility and sensitivity in the mass spectrometer. The mass marker used this invention could be readily introduced into a poly-ether polymer system as a sensitising group.

Poly-ethers can also be substituted with fluorine. This element is not common in biological materials and has advantageous features for mass spectrometry. An advantageous embodiment of this technology is the use of fluorinated mass labels when high resolution mass analysis of labels is employed after cleavage from their analyte, e.g. nucleic acid. A hydrogenated molecule whose integral mass is 100, will generally have a fractionally higher real mass when measured at very high resolution because hydrogen has a mass that is fractionally greater than 1 dalton. In contrast a fluorinated molecule whose integral mass is 100 will tend to have a fractionally lower real mass. These differences in mass are distinguishable in a high accuracy mass analysis and two molecules with the same integral mass but different compositions will produce distinct peaks in the mass spectrum if they have different degrees of hydrogenation and fluorination. Fluorinated molecules are said to a have a 'mass defect'. Since fluorinated molecules are not common in living systems, this means that a fluorinated mass label will be distinguishable in the mass spectrum even in the presence of contaminating peaks due to fragmentation of the nucleic acids or from buffers as long as the nucleic acids and reagents used are not fluorinated. Incorporation of a number of units of fluorinated aryl ethers is a simple means of introducing a mass defect into the mass label. This means that it is possible to assign a mass peak to a mass label rather than a contaminant if it has a mass defect.

It should be noted that this invention is not limited to the mass markers disclosed in PCT/GB98/00127. Any molecule with the correct features discussed above can be used as a mass marker.

The mass label used in this invention is preferably combined with a linker, L, that permits cleavage under mild conditions within the ion source of a mass spectrometer preferably generating only charged label species and neutral nucleic acid fragments. Linkers with the desired features are disclosed in UK applications 9815164.0 and 9815163.2. These applications disclose linkers that undergo gas phase cleavage and thermal and chemical cleavage reactions respectively. This permits the use of very mild ionisation conditions with ESI or FAB (see below) which reduces the levels of ionisation and fragmentation of contaminating material. Other linkers and mass markers that are appropriate for use with this invention are disclosed in PCT/GB98/00127.

The linkers used in the methods of the present invention are not especially limited, provided that they are cleavable. In a preferred embodiment of the present invention, L comprises a group having the following formula:

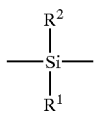

wherein $R^1$ and $R^2$ are substituents selected such that when the compound reacts with an electron donating moiety, either N or M cleaves from the Si atom in preference to $R^1$ and $R^2$. Preferably, $R^1$ and $R^2$ are selected such that each has a bond energy to Si greater than the bond energy of N and/or M to Si to ensure that when the compound reacts with an electron donating moiety either N or M cleaves from the Si atom in preference to $R^1$ and $R^2$, and/or $R^1$ and $R^2$ are selected such that their steric bulk is sufficient to ensure that when the compound reacts with an electron donatine moiety either N or M cleaves from the Si atom in preference to $R^1$ and $R^2$. It is particularly preferred that $R^1$ and $R^2$ are independently a hydrogen atom, a halogen atom, a substituted or unsubstituted alkyl group or a substituted or unsubstituted aryl group. Thus, $R^1$ and $R^2$ may each independently be fluorine, chlorine, bromine, iodine, methyl, ethyl, propyl, isopropyl, butyl, isobutyl, tert-butyl or phenyl groups.

In this embodiment of the present invention, the electron donating moiety used to cleave the linker is typically a Lewis base. Preferably the Lewis base is ammonia; a primary, secondary or tertiary amine; a compound containing a hydroxy group; an ether; or water.

In an alternative preferred embodiment of the present invention, L comprises a group having the following formula:

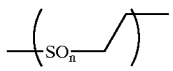

wherein n is 1 or 2.

A particularly preferred linker of this embodiment is one in which L comprises a group having the following formula:

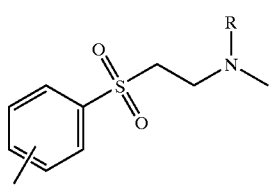

wherein R is an electron withdrawing substituent.

In this embodiment, it is preferred that R is a hydrogen atom, a halogen atom, or a substituent comprising a carbonyl group and/or a halogen atom. Thus, R may be a fluorine atom, a chlorine atom, a bromine atom, an iodine atom, a trifluoroacetyl group, or a trifluoromethyl acetate group.

In the embodiments of the present invention in which the linker comprises an $SO_n$ group, as shown above, it is preferred that the linker is cleaved by heating.

In the present invention, the analyte and the mass marker may, if desired, comprise a covalent linkage formed in attaching the analyte and/or mass marker to the cleavable linker. The covalent linkage is not particularly limited provided that the mass marker and/or the analyte can readily be attached to the cleavable linker using reactive functionalities attached to the linker and the mass marker and/or analyte. Typically, both the analyte and the mass marker comprise a covalent linkage, although in some embodiments only the analyte or only the mass marker comprises a covalent linkage.

Table 1 below lists some reactive functionalities that may be reacted together to generate a covalent linkage between two entities. Any of the functionalities listed below could be used to form the compounds used in the present invention to permit the linker to be attached to an analyte (such as a nucleic acid or protein) and to an appropriate mass marker group for detection. If desired, a reactive functionality can be used to introduce a further linking group with a further reactive functionality.

TABLE 1

| Functionality 1 | Functionality 2 | Resultant Covalent Linkage |
|---|---|---|
| —NH$_2$ | —COOH | —CO—NH— |
| —NH$_2$ | —NCO | —NH—CO—NH— |
| —NH$_2$ | —NCS | —NH—CS—NH— |
| —NH$_2$ | —CHO | —CH$_2$—NH— |
| —NH$_2$ | —SO$_2$Cl | —SO$_2$—NH— |
| —NH$_2$ | —CH=CH— | —NH—CH$_2$—CH$_2$— |
| —OH | —OP(NCH(CH$_3$)$_2$)$_2$ | —OP(=O)(O)O— |

It should be noted that some of the reactive functionalities above or their resultant covalent linkages might have to be protected prior to introduction into an oligonucleotide synthesiser. Preferably unprotected ether, ester, thioether and thioesters, amine and amide bonds are to be avoided as these are not stable in an oligonucleotide synthesiser. A wide variety of protective groups are known in the art to protect linkages from unwanted side reactions.

A short alkyl linkage would be appropriate to link the mass marker to the cleavable linker although a wide variety of linkers are available which can be used to link a mass marker to the tertiary amine croup of the linker.

Thus, in preferred embodiments of the present invention, the covalent linkage attaching the cleavable linker to the mass marker group and/or the analyte is independently selected from a —CO—NH— group, an —NH—CO—NH— group, an —NH—CS—NH— group, a —CH$_2$—NH— group, an —SO$_2$—NH— group, an —NH—CH$_2$—CH$_2$— group, or an —OP(=O)(O)O— group.

Mass Spectrometry Features

The most important features of a mass spectrometer are as follows:

Inlet System->Ion Source->Mass Analyser->Ion Detector->Data Capture System

For the purposes of analysing biomolecules, which for this application are typically mass labelled nucleic acids, the inlet system and ion source are particularly important features of the mass spectrometer. Other features of importance for the purposes of biological analysis are the sensitivity of the mass analyser/detector arrangements and their ability to quantify analyte molecules. Some favourable mass analysers are discussed in PCT/GB98/00127.

Ionisation Techniques

For many biological mass spectrometry applications so called 'soft' ionisation techniques are used. These allow large molecules such as proteins and nucleic acids to be ionised essentially intact The liquid phase techniques allow large biomolecules to enter the mass spectrometer in solutions with mild pH and at low concentrations. A number of techniques are ideal for use with this invention including but not limited to Electrospray ionisation, Fast Atom Bombardment and Matrix Assisted Laser Desorption Ionisation (MALDI).

Electrospray Ionisation

Electrospray ionisation requires that the dilute solution of biomolecule be nebulised into the ion source of a mass spectrometer, i.e. injected as a fine spray. The solution is, for example, sprayed from the tip of a needle in a stream of dry nitrogen and an electrostatic field. The mechanism of ionisation is not fully understood but is thought to work broadly as follows. In the stream of nitrogen the solvent is evaporated. With a small droplet, this results in concentration of the biomolecule. Given that most biomolecules have a net charge this increases the electrostatic repulsion of the dissolved protein. As evaporation continues this repulsion ultimately becomes greater than the surface tension of the droplet and the droplet explodes into smaller droplets. The electrostatic field helps to further overcome the surface tension of the droplets and assists in the spraying process. The evaporation continues from the smaller droplets which, in turn, explode iteratively until essentially the biomolecules are in the vapour phase, as is all the solvent. This technique is of particular importance in the use of mass labels in that the technique imparts a relatively small amount of energy to ions in the ionisation process and the energy distribution within a population tends to fall in a narrower range when compared with other techniques. The ions are accelerated out of the ionisation chamber through a pair of electrodes. The potential difference across these electrodes determines whether positive or negative ions pass into the mass analyser and also the energy with which these ions enter the mass spectrometer. This is of significance when considering fragmentation of ions in the mass spectrometer. The more energy imparted to a population of ions the more likely it is that fragmentation will occur through collision of analyte molecules with the bath gas present in the source. By adjusting the accelerating voltage used to accelerate ions from the ionisation chamber one can control the fragmentation of ions and, to some extent, the degree of ionisation. For the purposes of this invention fragmentation and ionisation of nucleic acids and background contaminants is preferably avoided. ESI is advantageous for this purpose in that fragmentation can be greatly reduced by accelerating ions through the ion source with a relatively low cone voltage.

Matrix Assisted Laser Desorption Ionisation (MALDI)

MALDI requires that the biomolecule solution be embedded in a large molar excess of a photo-excitable matrix. The application of laser light of the appropriate frequency (266 nm beam for nicotinic acid) results in the excitation of the matrix which in turn leads to excitation and ionisation of the embedded biomolecule. This technique imparts a significant quantity of translational energy to ions, but tends not to induce excessive fragmentation despite this Accelerating voltages can again be used to control fragmentation with this technique though.

MALDI techniques can be supported in two ways. One can embed mass labelled DNA in a MALDI matrix, where the labels themselves are not specifically excitable by laser or one can construct labels that contain the necessary groups to allow laser energisation. The latter approach means the labels do not need to be embedded in a matrix before performing mass spectrometry. Such groups include nicotinic, sinapinic or cinnamic acid moieties. MALDI based cleavage of labels is most effective with a photocleavable linker as this avoids a cleavage step prior to performing MALDI mass spectrometry. The various excitable ionisation agents have different excitation frequencies so that a different frequency can be chosen to trigger ionisation from that used to cleave the photocleavable linker. These excitable moieties are easily derivitised using standard synthetic techniques in organic chemistry so labels with multiple masses can be constructed in a combinatorial manner.

Fast Atom Bombardment

Fast Atom Bombardment (FAB) has come to describe a number of techniques for vaporising and ionising relatively involatile molecules. The essential principal of these techniques is that samples are desorbed from surfaces by collision of the sample with accelerated atoms or ions, usually xenon atoms or caesium ions. The samples may be coated onto a solid surface as for MALDI but without the requirement of complex matrices. These techniques are also compatible with liquid phase inlet systems—the liquid eluting from a capillary electrophoresis inlet or a high pressure liquid chromatography system pass through a frit, essentially coating the surface of the frit with analyte solution which can be ionised from the frit surface by atom bombardment. FAB is known to fetch pre-ionised material from the frit surface with high efficiency and is thus likely to be another highly favoured inlet and ionisation procedure.

What is claimed is:

1. A compound having the following formulas:

wherein N comprises an analyte, L comprises a cleavable linker between N and M, and M comprises a mass marker having a metal ion binding moiety.

2. The compound according to claim 1, wherein the metal ion-binding moiety is selected from the group consisting of a porphyrin, a crown ether, hexahistidine, and a multidentate ligand.

3. The compound according to claim 1, wherein the metal ion-binding moiety is a bidentate ligand or is EDTA.

4. The compound according to claim 1, wherein the metal ion-binding moiety is bound to a member selected from the group consisting of a monovalent metal ion, a divalent metal ion, and a trivalent metal ion.

5. The compound according to claim 4, wherein the metal ion is selected from the group consisting of a transition metal ion, a metal ion of group IA, a metal ion of group IIA, and a metal ion of group IIIA of the periodic table.

6. The compound according to claim 4, wherein the metal ion is selected from the group consisting of $Ni^{2+}$, $Li^+$, $Na^+$, $K^+$, $Mg^{2+}$, $Ca^{2+}$, $Sr^{2+}$, $Ba^{2+}$, and $Al^{3+}$.

7. The compound according to claim 1, wherein the analyte (N) is selected from the group consisting of a nucleotide, an oligonucleotide, and a nucleic acid base.

8. The compound according to claim 7, wherein the nucleotide, oligonucleotide, or nucleic acid base is natural or modified by modifying a base, sugar and/or backbone of the nucleotide, oligonucleotide, or nucleic acid base.

9. The compound according to claim 1, wherein the mass marker (M) comprises a substituted or unsubstituted polyether.

10. The compound according to claim 9, wherein the polyether is a substituted or unsubstituted poly(arylether).

11. The compound according to claim 9, wherein the polyether comprises at least one substituent selected from the group consisting of a fluorine atoma, methyl group, $^2H$ and $^{13}C$ isotopic substituents.

12. The compound according to claim 1, wherein the cleavable linker (L) comprises a group having the following formula:

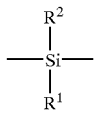

wherein $R^1$ and $R^2$ are substituents selected such that when the compound reacts with an electron donating moiety, either N or M cleaves from the Si atom in preference to $R^1$ and $R^2$.

13. The compound according to claim 12, wherein $R^1$ and $R^2$ are selected such that each has a bond energy to Si greater than the bond energy of at least one of N, M to Si to ensure that when the compound reacts with an electron donating moiety, either N or M cleaves from the Si atom in preference to $R^1$ and $R^2$, at least one of $R^1$ and $R^2$ are selected such that their steric bulk is sufficient to ensure that when the compound reacts with an electron donating moiety either N or M cleaves from the Si atom in preference to $R^1$ and $R^2$.

14. The compound according to claim 12, wherein $R^1$ and $R^2$ are selected from the group consisting of a hydrogen atom, a substituted alkyl group, an unsubstituted alkyl group, a substituted aryl group, and an unsubstituted aryl group.

15. The compound according to claim 12, wherein $R^1$ and $R^2$ are selected from the group consisting of a fluorine atom, a chlorine atom, a bromine atom, an iodine atom, a methyl group, an ethyl group, a propyl group, an isopropyl group, a butyl group, an isobutyl group, a tert-butyl group, and a phenyl group.

16. The compound according to claim 13, wherein the electron donating moiety is a Lewis base.

17. The compound according claim 16, wherein the Lewis base is selected from the group consisting of ammonia, a primary amine, a secondary amine, a tertiary amine, a compound containing a hydroxyl group, an ether, and water.

18. The compound according claim 1, wherein the cleavable linker (L) comprises a group having the following formula:

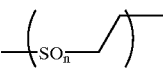

wherein n is 1 or 2.

19. The compound according to claim 1, wherein L comprises a group having the following formula:

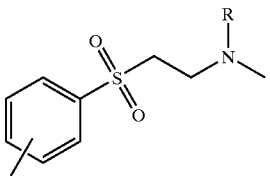

wherein R is an electron withdrawing substituent.

20. The compound according to claim 19, wherein R is selected from the group consisting of a hydrogen atom, a halogen atom, a substituent comprising a carbonyl group, a substituent comprising a halogen atom, and a substituent comprising a carbonyl group and/or a halogen atom.

21. The compound according to claim 19, wherein R is selected from the group consisting of a fluorine atom, a chlorine atom, a bromine atom, an iodine atom, a trifluoroacetyl group, and a trifluoromethyl acetate group.

22. The compound according to claim 1, wherein L is attached to at least one of N and M by a member selected from the group consisting of a —CO—NH— group, an —NH—CO—NH— group, a —CH$_2$—NH— group, an —SO$_2$—NH— group, an —NH—CH$_2$—CH$_2$— group, and an —OP(=O)(O)O— group.

23. A method for characterising an analyte that comprises:
(a) providing a compound in which the analyte (N) is attached by a cleavable linker (L) to a mass marker (M) relatable to the analyte;
(b) cleaving the mass marker from the analyte; and
(c) identifying the mass marker, thereby characterising the analyte wherein the mass marker comprises a metal ion-binding moiety.

24. The method according to claim 23, wherein the metal ion-binding moiety is selected from the group consisting of a porphyrin, a crown ether, hexahistidine, and a multidentate ligand.

25. The method according to claim 23, further comprising binding of a monovalent, divalent, or trivalent metal ion to the metal ion-binding moiety, prior to identifying the mass marker by mass spectroscopy.

26. The method according to claim 23, wherein the mass marker comprises a substituted or unsubstituted polyether.

27. The method according to claim 23, further comprising forming a compound having the following formula:

wherein N comprises a nucleic acid, L comprises a cleavable linker between N and M, and M comprises a mass marker having a metal ion binding moiety, prior to identifying the mass marker.

28. The method according to claim 27, wherein the cleavable linker (L) is a member selected from the group consisting of

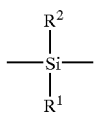

wherein R¹ and R² are substituents selected such that when the compound reacts with an electron donating moiety, either N or M cleaves from the Si atom in preference to R¹ and R²;

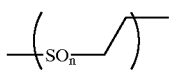

wherein n is 1 or 2; and

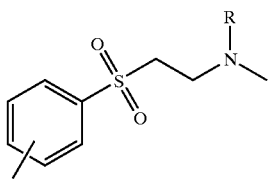

wherein R is an electron withdrawing substituent.

29. The method according to claim 28, further comprising contacting the compound with an electron-donating moiety to cleave the mass marker (M) from the compound.

30. The method according to claim 29, wherein the electron-donating moiety is a metal ion selected from the group consisting of $Ni^{2+}$, $Li^+$, $Na^+$, $K^+$, $Mg^{2+}$, $Ca^{2+}$, $Sr^{2+}$, $Ba^{2+}$, and $Al^{3+}$.

31. The method according to claim 23, wherein L is member selected from the group consisting of

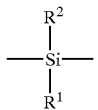

wherein R¹ and R² are substituents selected such that when the compound reacts with an electron donating moiety, either N or M cleaves from the Si atom in preference to R¹ and R²;

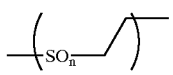

wherein n is 1 or 2; and

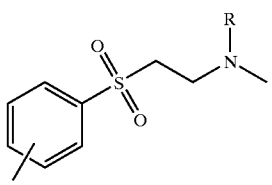

wherein R is an electron withdrawing substituent.

32. The method according to claim 31, further comprising heating the compound to cleave the mass marker from the molecule.

33. The method according to claim 23, wherein the mass marker is cleaved from the compound in a mass spectrometer.

34. The method according to claim 23, wherein N is selected from the group consisting of a protein, a polypeptide, an amino acid, a nucleic acid, a nucleic acid base, a pharmaceutical agent or drug, a carbohydrate, a lipid, a natural product, and a synthetic compound from an encoded chemical library.

35. The method according to claim 27, wherein the mass marker (M) is identifiable by mass spectrometry, comprises a metal ion-binding moiety, and is cleavably linked to the analyte.

36. The method according to claim 35, wherein the metal ion-binding moiety is selected from the group consisting of a porphyrin, a crown ether, hexahistidine, and a multidentate ligand.

37. The method according to claim 35, wherein the analyte is selected from the group consisting of a protein, a polypeptide, an amino acid, a nucleic acid, a nucleic acid base, a pharmaceutical agent or drug, a carbohydrate, a lipid, a natural product, and a synthetic compound from an encoded chemical library.

38. The method according to claim 35, wherein M comprises a substituted or unsubstituted polyether.

39. The method according to claim 35, wherein M is attached to the N by L, wherein L is selected from the group consisting of a structure having the following generic structure:

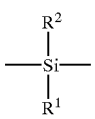

wherein R¹ and R² are substituents selected such that when the compound reacts with an electron donating moiety, either N or M cleaves from the Si atom in preference to R¹ and R²

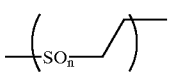

wherein n is 1 or 2; and

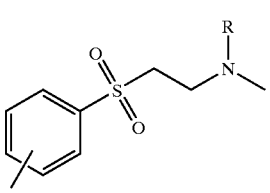

wherein R is an electron withdrawing substituent.

* * * * *

UNITED STATES PATENT AND TRADEMARK OFFICE
CERTIFICATE OF CORRECTION

PATENT NO. : 6,582,916 B1 Page 1 of 1
DATED : June 24, 2003
INVENTOR(S) : Gunter Schmidt et al.

It is certified that error appears in the above-identified patent and that said Letters Patent is hereby corrected as shown below:

<u>Title page</u>,
Item [73], Assignee, replace "Aventis Research & Technologies GmbH & Co. KG, Frankfurt (DE)" with -- Xzillion GmbH & Co. KG, Frankfurt (DE) --.

Signed and Sealed this

Twentieth Day of April, 2004

JON W. DUDAS
*Acting Director of the United States Patent and Trademark Office*